(12) United States Patent
Hlavacek et al.

(10) Patent No.: US 8,401,797 B2
(45) Date of Patent: Mar. 19, 2013

(54) METHOD FOR PREDICTING ENZYME-CATALYZED REACTIONS

(75) Inventors: William S. Hlavacek, Santa Fe, NM (US); Clifford J. Unkefer, Los Alamos, NM (US); Fangping Mu, Los Alamos, NM (US); Pat J. Unkefer, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1420 days.

(21) Appl. No.: 11/862,103

(22) Filed: Sep. 26, 2007

(65) Prior Publication Data

US 2008/0177478 A1    Jul. 24, 2008

Related U.S. Application Data

(60) Provisional application No. 60/827,362, filed on Sep. 28, 2006.

(51) Int. Cl.
*G01N 33/48* (2006.01)
(52) U.S. Cl. ......................................................... 702/19
(58) Field of Classification Search .................... 702/19
See application file for complete search history.

(56) References Cited

U.S. PATENT DOCUMENTS

| 2003/0125548 | A1* | 7/2003 | Arad et al. ................. | 544/59 |
| 2008/0033899 | A1* | 2/2008 | Barnhill et al. ............ | 706/48 |
| 2008/0059077 | A1* | 3/2008 | Zhou et al. ................. | 702/19 |

OTHER PUBLICATIONS

F. Darvas, "Predicting metabolic pathways by logic programming", Journal of Molecular Graphics, 1988, pp. 80-86, vol. 6.
N. Greene et al., "Knowledge-Based Expert Systems for Toxicity and Metabolism Prediction: DEREK, StAR and METEOR", SAR and QSAR in Environmental Research, 1999, pp. 299-314, vol. 10.
G. Klopman et al., "META. 1. A Program for the Evaluation of Metabolic Transformation of Chemicals", Journal of Chemical Information and Computer Science, 1994, pp. 1320-1325, vol. 34.
J. Talafous et al., "META. 2. A Dictionary Model of Mammalian Xenobiotic Metabolism", Journal of Chemical Information and Computer Science, 1994, pp. 1326-1333, vol. 34.
B.K. Hou et al., "Microbial Pathway Prediction: A Functional Group Approach", Journal of Chemical Information and Computer Science, 2003, pp. 1051-1057, vol. 43.
D.C. McShan et al., "Symbolic Interference of Xenobiotic Metabolism", Pacific Symposium on Biocomputing, 2004, pp. 545-556, vol. 9.
V. Hatzimanikatis et al., "Exploring the biodiversity of complex metabolic works", Bioinformatics, 2005, pp. 1603-1609, vol. 21, No. 8.

* cited by examiner

*Primary Examiner* — Jerry Lin
(74) *Attorney, Agent, or Firm* — John P. O'Banion

(57) ABSTRACT

The reactivity of given metabolites is assessed using selected empirical atomic properties in the potential reaction center. Metabolic reactions are represented as biotransformation rules. These rules are generalized from the patterns in reactions. These patterns are not unique to reactants but are widely distributed among metabolites. Using a metabolite database, potential substructures are identified in the metabolites for a given biotransformation. These substructures are divided into reactants or non-reactants, depending on whether they participate in the biotransformation or not. Each potential substructure is then modeled using descriptors of the topological and electronic properties of atoms in the potential reaction center; molecular properties can also be used. A Support Vector Machine (SVM) or classifier is trained to classify a potential reactant as a true or false reactant using these properties.

20 Claims, 17 Drawing Sheets

BIOTRANSFORMATION FOR OXIDOREDUCTASES

| Reaction type | Major EC number | # of rxns |
|---|---|---|
| Dehydrogenation of primary alcohol | 1.1 | 169 |
| Dehydrogenation of secondary alcohol | 1.1 | 424 |
| Dehydrogenation of heme-acetal | 1.1 | 34 |
| Aldehyde oxidation | 1.2 | 175 |
| Oxo oxidation | 1.2 | 35 |
| Dehydrogenation of CH-CH to C=C | 1.3 | 258 |
| Dehydrogenation of primary amine to C=O | 1.4 | 90 |
| Dehydrogenation of secondary amine to C=N | 1.5 | 46 |
| Hydroxylation of CH | 1.14 & 1.17 | 202 |
| Hydroxylation of CH (aromatic) | 1.14 | 147 |
| Hydroxylation of xanthine and similar | 1.17 | 14 |
| Dihydroxylation and epoxidation | 1.14 | 103 |
| Dioxygenase (aromatic) | 1.13 | 75 |
| Oxidation to form C-halide | 1.97 | 30 |
| Dealkylation (include O, N-dealkylation) (product 1 is aldehyde or ketone and product 2 is amine or alcohol) | 1.5 & 1.14 | 52 |
| Nitro oxidation | 1.7 | 39 |
| Oxidation of SH group to S-S group | 1.8 | 33 |
| Sulfur oxidation | 1.8 | 26 |
| Oxidation to quinone | 1.6 & 1.14 | 19 |
| Adding O to C-C | 1.14 | 19 |
| Oxidative cleaving $CO_2$ | 1.14 & 1.13 | 33 |

FIG. 6A

BIOTRANSFORMATION FOR TRANSFERASES

| Reaction type | Major EC number | # of rxns |
|---|---|---|
| Methyl transfer with N acceptor | 2.1.1 | 56 |
| Methyl transfer with O acceptor | 2.1.1 | 124 |
| Methyl transfer with C acceptor | 2.1.1 | 27 |
| Methyl transfer with S acceptor | 2.1.1 | 16 |
| Hydroxymethyl-, Formyl and related transfer | 2.1.2 | 14 |
| Carboxy-, Carbamoyl- and amidino transfer | 2.1.3 & 4 | 15 |
| Aldehyde, Ketonic transfer | 2.2 | 20 |
| Acyl transfer with O acceptor | 2.3.1&2 | 150* |
| Acyl transfer with S acceptor | 2.3.1&2 | 189* |
| Acyl transfer with N acceptor | 2.3.1&2 | 95* |
| Acyl transfer with C acceptor | 2.3.1&2 | 32 |
| Acyl to alkyl (product 1 is with CoA group and | 2.3.3 | 14 |
| Hexosyl and related transfer with O acceptor | 2.4.1&99 | 241 |
| Pentosyl transfer | 2.4.2 | 44 |
| Glutathione transfer | 2.5.1.18 | 20 |
| Diphosphate related Alkyl transfer | 2.5.1 | 27 |
| Amino acide and related transfer | 2.5.1 | 23 |
| Nitrogenous | 2.6 | 113 |
| Phospho transfer with alcohol acceptor | 2.7.1 | 231 |
| Phospho transfer with carboxy acceptor | 2.7.2 | 17 |
| Phospho transfer with nitrogenous acceptor | 2.7.3 | 13 |
| Phospho transfer with phosphate acceptor | 2.7.4 | 38 |
| Transfer other substituted phosphate groups | 2.7.8 | 28 |
| Nucleotidyl transfer | 2.7.7 | 52 |
| Sulfo transfer | 2.8.2 | 28 |
| CoA transfer | 2.8.3 | 27 |

FIG. 6B

BIOTRANSFORMATION FOR HYDROLASES

| Reaction type | Major EC number | # of rxns |
|---|---|---|
| Linear carboxylic ester (product 1 is carboxyl acid and product 2 is alcohol) | 3.1.1 | 74 |
| Cyclic carboxylic ester | 3.1.1 | 39 |
| Thiolester | 3.1.2 | 25 |
| Phosphoric, diphosphoric or triphosphoric monoester hydrolyzation | 3.1.3&5&7 | 110 |
| Linear phosphoric diester or trimester hydrolyzation (product 1 is alcohol and product 2 is with phosphoric group) | 3.1.4&8 | 28 |
| Cyclic phosphoric diester hydrolyzation | 3.1.4 | 11 |
| Sulfuric ester | 3.1.6 | 13 |
| O-glycosyl hydrolyzation | 3.2.1 | 83 |
| N-glycosyl hydrolyzation | 3.2.2 | 21 |
| Epo-hydrolyzation | 3.3 | 26 |
| Linear amides (product 1 is carboxyl acid and product 2 is amide) | 3.4 & 3.5.1 | 141 |
| Cyclic amides | 3.5.2 | 24 |
| Linear amidines | 3.5.3 | 16 |
| Cyclic amidines | 3.5.4 | 33 |
| Cyclic Imine | 3.5.4 | 26 |
| Nitriles | 3.5.5 | 11 |
| Acid anhydrides (product 1 is with phosphorous acid group and product 2 is the other acid) | 3.6 | 74 |
| C-C hydrolyzation acting on ketonic substances (product 1 is carboxyl acid and the other product is product 2) | 3.7.1 | 31 |
| C-halide hydrolyzation | 3.8 | 25 |

FIG. 6C

BIOTRANSFORMATION FOR LYASES

| Reaction type | Major EC number | # of rxns |
|---|---|---|
| Remove CO2 | 4.1.1 | 151 |
| Aldehyde lyases (product 1 is aldehyde and the other product is product 2) | 4.1.2 | 57 |
| Oxo-acid lyases (product 1 is ketone and the other product is product 2) | 4.1.3 | 19 |
| C-O lyases to C=C | 4.2 | 101 |
| C-(N,S,halide) lyases to C=C | 4.3&4&5 | 24 |
| C-(O,N,S,halide) lyases to C-C=O | 4.2&3&4&5 | 58 |
| Lyases to C#(C,N) | 4.2 | 16 |

FIG. 6D

BIOTRANSFORMATION FOR ISOMERASES

| Reaction type | Major EC number | # of rxns |
|---|---|---|
| Interconverting Aldoses and Ketoses | 5.3.1 | 29 |
| Transposing C=C (reactant and product are analyzed together) | 5.3.3 | 44 |
| Intermolecular C-O lyases | 5.5.1 | 25 |

FIG. 6E

BIOTRANSFORMATION FOR LIGASES

| Reaction type | Major EC number | # of rxns |
|---|---|---|
| Acid-Thiol ligases | 6.2 | 68 |
| Acid-Amonia, amine or amino ligases (reactant 1 is carboxyl acid and reactant 2 is amide) | 6.3.1&2&5 | 80 |
| Other C-N ligases (reactant 1 is with the accepting C group and reactant 2 is amide) | 6.3.3&4 | 15 |
| Forming C-C bond (reactant 2 is with accepting C group and reactant 1 is with donor carboxyl or $CO_2$ group) | 6.4 | 9 |

FIG. 6F

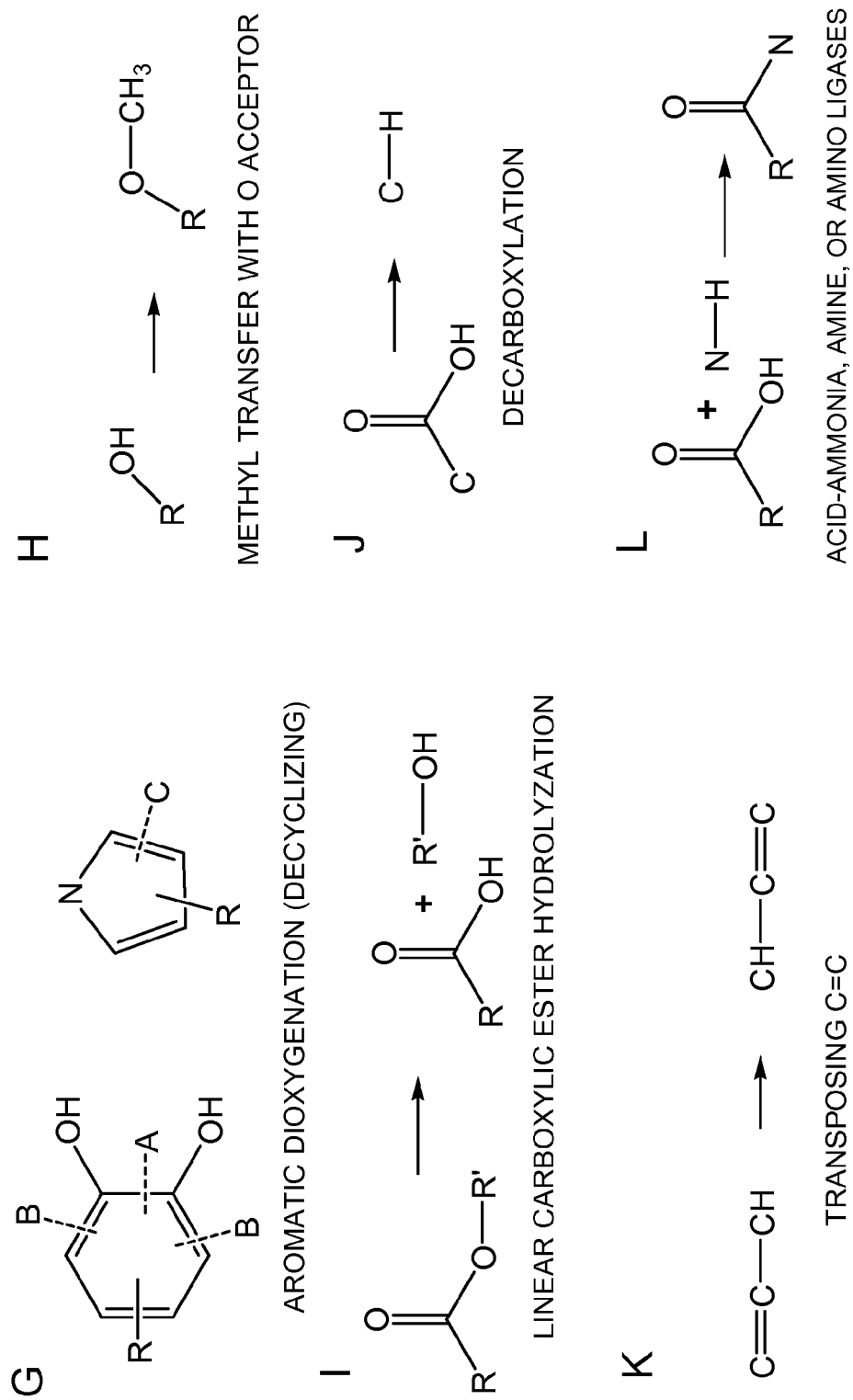
FIG. 6 G-L

ATOMIC PROPERTIES

| |
|---|
| Electrogeometrical state index |
| Electrotopological state index |
| Conjugated electrotopological state index |
| Graph potentials |
| Gasteiger Marsili Partial Charges |
| Effective Polarizability |
| Sigma Electronegativity |
| Numerical AccessibleArea |
| Inductive Partial Charge |
| Effective Atomic Electronegativity |
| Inductive Atomic Hardness |
| Inductive Atomic Softness |
| $D_n(r)$ |
| $D_e(r)$ |
| $q(r)-Z(r)$ |
| $piS(r)$ |
| contribution to homo |
| contribution to lumo |
| net charge |
| s-pop |
| p-pop |

FIG. 7A

MOLECULAR PROPERTIES

| |
|---|
| LogP |
| 3 Kier Shape |
| Refractivity |
| Topological Polar Surface Area |
| 29 Charged Partial Surface Area |
| Numerical Surface Area |
| 6 properties based on MOPAC (Ionization Potential; Mulliken Electronegativity; Parr & Pople Absolute Hardness; Schuurmann alpha MO shift; Ehomo; Elumo) |

METHOD FOR PREDICTING ENZYME-CATALYZED REACTIONS

CROSS-REFERENCE TO RELATED APPLICATIONS

This application claims priority from U.S. provisional patent application Ser. No. 60/827,362 filed on Sep. 28, 2006, incorporated herein by reference in its entirety.

STATEMENT REGARDING FEDERALLY SPONSORED RESEARCH OR DEVELOPMENT

This invention was made with Government support under Contract No. DE-AC52-06NA25396, awarded by the Department of Energy. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C. F. R. §1.14.

BACKGROUND OF THE INVENTION

1. Field of the Invention

This invention pertains generally to bioinformatics and to knowledge-based expert systems, and more particularly to the prediction of enzyme-catalyzed chemical reactions.

2. Description of Related Art

Although our knowledge of metabolism is extensive, it is still incomplete. Many metabolites present in cells, and their reactions and associated enzymes, remain to be discovered. Systematic and rapid approaches for determining how a newly discovered metabolite is produced and consumed are lacking. Thus, a present challenge for bioinformatics in support of metabolomics is the development of computational methods that will help place novel metabolites in the context of biochemical pathways efficiently and accurately.

The prediction of metabolic reactions has been a topic of interest for some time, in part because the metabolic breakdown products of a drug can sometimes be toxic. Bioremediation is another area in which predictive understanding of metabolic breakdown products is important. Because enzyme-catalyzed reactions are generally too complex to be predicted from first principles, a variety of knowledge-based expert systems have been developed for predicting metabolic transformations, and several software tools are available for the prediction of biodegradation pathways, such as MetabolExpert, METEOR, and META. These systems are based on expert-defined rules for biotransformations that generalize the transformations of known reactions. For example, a recently developed system, BNICE, is based on around 250 enzyme-reaction rules derived from the Enzyme Commission (EC) classification system. The rules are essentially generators of chemical reactions, and they are applied to enumerate the reactions in which a molecule of interest may potentially participate. The number of rules varies from system to system [cf., META, which is based on 1118 rules]. The number of rules reflects the level of abstraction judged to be appropriate, the intended scope of application, and the data considered when formulating the rules.

A common problem of systems for rule-based reaction prediction is the number of false positives. Given a molecule, rule application tends to generate a large number of possible reactions, and a combinatorial explosion occurs if rules are applied iteratively to the products of predicted reactions. To mitigate this problem, researchers have attempted to use expert knowledge to limit the generality of rules. Some systems provide priority indices or other filters based on expert knowledge to aid a user in assessing the likelihood of a reaction.

Our knowledge of metabolism is far from complete, and the gaps in our knowledge are being revealed by metabolomic detection of small-molecules not previously known to exist in cells. An important challenge is to determine the reactions in which these compounds participate, which can lead to the identification of gene products responsible for novel metabolic pathways. To address this challenge, the present invention uses machine learning to predict potential substrates and products of enzyme-catalyzed reactions.

To find new therapeutics, drug developers are scanning many compounds. Failure of a drug candidate in a late testing phase is very costly, so a "fail-fast, fail-cheap" approach has been widely adopted, in which various properties, including metabolism, are studied at the early stage of drug development. In silico tools enable fast and virtual screening of large numbers of compounds, so that poor candidates can be eliminated up front. Actual assays are then performed from the short-listed pool of compounds increasing the success rate of finding a good candidate with desirable characteristics.

BRIEF SUMMARY OF THE INVENTION

The invention is an extension of rule-based reaction prediction by incorporating the use of machine learning. For a given chemical structure, potential reaction centers of the biotransformation are identified through molecular structure matching. For each potential reaction center, a set of descriptors selected from chemical properties and features, including atomic features and molecular features, are calculated. Based on a pretrained model using these descriptors, a binary or probability number is given to assess the reactivity potential that the reaction center will perform the given biotransformation. The focus of an illustrative preferred embodiment is on oxidoreductase-catalyzed reactions, which account for more than one third of all known enzymatic reactions documented in the KEGG database, but the invention can be generalized to other reactions and data from other chemical databases. Using information about reactions and metabolites available in KEGG, a Support Vector Machine (SVM) is trained to classify a potential reactant in an oxidoreductase-catalyzed reaction as a true or false reactant. The classification is based on seven quantitative structure-property relationship (QSPR) descriptors. Twelve (12) classes of reactions, which are marked by characteristic functional group transformations, were considered. These reaction classes correspond more or less to subclasses of the EC 1 class of enzymes.

A large number (1956) of oxidation/reduction reactions in the KEGG database were examined. The vast majority of these reactions (1626) can be divided into twelve subclasses, each of which is marked by a particular type of functional group transformation. For a given transformation, the local structures of reaction centers in substrates and products can be characterized by patterns. These patterns are not unique to reactants but are widely distributed among KEGG metabolites. To distinguish reactants from non-reactants, classifiers (linear kernel Support Vector Machines) were trained using negative and positive examples. The input to a classifier is a set of atomic features that can be determined from the 2D chemical structure of a compound. Depending on the subclass of reaction, the accuracy of prediction for positives (negatives) is 64 to 93% (44 to 92%) when asking if a compound is a substrate and 71 to 98% (50 to 92%) when asking if a compound is a product. Sensitivity analysis reveals that this performance is robust to variations of the training data. The results suggest that metabolic connectivity can be predicted with reasonable accuracy from the presence or absence of local structural motifs in compounds and their readily calculated atomic features.

An aspect of the invention is a method of predicting the reactivity of a metabolite, by obtaining information about a class of metabolic chemical reactions; dividing the class of reactions into a plurality of subclasses, each marked by a particular type of functional group transformation; determining local structures of reaction centers for each transformation; defining a set of reaction center patterns from the local structures; and determining if the metabolite is a potential reactant in a subclass by determining if it has structural features compatible with a subclass-specific reaction center using a trained classifier. Determining if the metabolite has structural features compatible with a subclass-specific reaction center using a trained classifier can be done by training a classifier for each transformation; calculating a set of descriptors selected from atomic properties for each atom in a reaction center and molecular properties; inputting the set of descriptors to the classifier; and predicting the reactivity of the metabolite to participate in a reaction.

Another aspect of the invention is a system for predicting the reactivity of a metabolite, including a processor for receiving information about a class of metabolic chemical reactions; dividing the class of reactions into a plurality of subclasses, each marked by a particular type of functional group transformation; determining local structures of reaction centers for each transformation; and defining a set of reaction center patterns from the local structures; a classifier for predicting the reactivity of the metabolite to participate in a reaction, the classifier having been trained for each transformation; and a descriptor calculator for calculating a set of descriptors selected from atomic properties for each atom in a reaction center and molecular properties, the set of descriptors being input to the trained classifier.

A further aspect of the invention is a system for predicting the reactivity of a metabolite, including a processor for receiving information about a class of metabolic chemical reactions; dividing the class of reactions into a plurality of subclasses, each marked by a particular type of functional group transformation; determining local structures of reaction centers for each transformation; and defining a set of reaction center patterns from the local structures; and means for determining if the metabolite is a potential reactant in a subclass by determining if it has structural features compatible with a subclass-specific reaction center.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 6A-F show the classifications of reactions catalyzed by different types of enzymes (different EC classes).

FIG. 6G-L illustrate biotransformations for each of the six EC classes.

FIG. 7A-B are lists of different atomic and molecular properties that can be used for reaction classification.

DETAILED DESCRIPTION OF THE INVENTION

Figure 1:
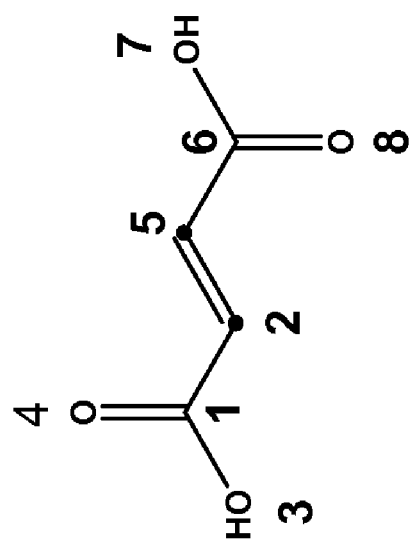
FIG. 1 shows a reaction center for a class 3 reaction.
Figure 1:
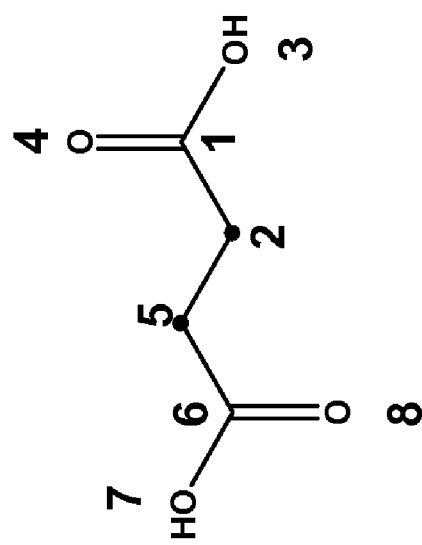

Referring more specifically to the drawings, for illustrative purposes the present invention is embodied in the data, chemical structures, flowcharts and system diagrams generally shown in FIG. 1 through FIG. 9. It will be appreciated that the method may vary as to sequence and details of the steps and as to specific data used, and the apparatus may vary as to configuration and as to details of the parts, without departing from the basic concepts as disclosed herein.

The invention applies to the assessment of the reactivity of given metabolites using features to model the atoms in the reaction centers and features to model the whole molecule. Metabolic reactions are represented as biotransformation rules. These rules are generalized from the patterns in reactions. These patterns are not unique to reactants but are widely distributed among metabolites. Using a metabolite database, such as KEGG and MDL's Metabolite®, potential substructures are identified in the metabolites for a given biotransformation. These substructures are divided into reactants or non-reactants, depending on whether they participate in the biotransformation or not. Each potential substructure is then modeled using descriptors selected from the topological and electronic properties of atoms in the potential reaction center and molecular properties. A Support Vector Machine (SVM) or classifier is trained to classify a potential reactant as a true or false reactant using these properties. A particular preferred embodiment implemented using the KEGG metabolite database utilizes patterns in reactions with the same Enzyme Commission (EC) numbers up to second or third level (specifically oxidoreductase catalyzed reactions), but the invention is not limited to this specific example.

A. Methodology

A. 1. Data

An illustrative embodiment of the invention utilizes the KEGG LIGAND composite database, which on Dec. 8, 2005, contained information about 6455 reactions, of which 4993 are associated with a full EC number and 537 are associated with a partial EC number. These 5530 reactions involve a total of 4139 distinct metabolites as substrates, products, or cofactors. For each of these metabolites, its associated MDL Molfile (if available) was downloaded from the COMPOUND section of the database. This file encodes the 2D chemical structure except for hydrogen atoms, which are usually missing. To obtain complete structures, hydrogen atoms were added consistent with valency using CDK and JOELib. Chirality and other 3D structural features of the metabolites were not considered; the results are unaffected because classifications are made on the basis of descriptors that depend only on 2D chemical structure (see below). Of the 5530 reactions with EC information, 1956 are classified as oxidoreductase-catalyzed reactions (i.e., assigned an EC 1.-.-.-number). Information available about each of these reactions was downloaded from the REACTION section of the database. In some cases, a metabolite in a reaction is indicated as having a generic R group. An example is the reaction with KEGG reference number R04429. In these cases, the R group was replaced with the simplest possible alkane group, which was usually a methyl group (—CH3).

A.2. Reaction Classification Based on Functional Group Chemistry

Oxidoreductases catalyze oxidation and reduction reactions, which involve electron transfer from one metabolite to another. In the Enzyme Commission classification scheme, oxidoreductase-catalyzed reactions are divided into 22 subclasses based on the donor group that undergoes oxidation. Sub-subclasses are defined based on the acceptor group.

This illustrative embodiment of the invention utilizes the 12 classes of oxidoreductase-catalyzed reactions listed in Table 1, which were defined based on functional group transformations of substrates, ignoring cofactors, such as NAD(P)$^+$, FAD$^+$, and O$_2$. These classes largely correspond to EC 1 subclasses, though the correspondence is not 1-to-1. The 12 classes include 1626 of the 1956 oxidoreductase-catalyzed reactions in KEGG. The other 330 reactions, which were not considered further, are exotic (e.g., they involve oxidation of a metal ion, sulfur group, or cofactor) or, in 114 cases, involve metabolites for which structural information is unavailable from KEGG. Most of the 1626 reactions classified in Table 1 belong to one of the 10 most populated EC 1 subclasses, which are 1.1, 1.2, 1.3, 1.4, 1.5, 1.7, 1.8, 1.13, 1.14, and 1.17. Within each of these EC subclasses, reactions tend to involve a particular functional group transformation or set of transformations, although there are a few exceptions (e.g., reaction R02260 in KEGG, which is assigned EC 1.2.1.49, is better placed in Class 1 of Table 1 rather than Class 2 like other EC 1.2.-.- reactions). Reactions in EC 1.14, which involve paired donors and incorporation of molecular oxygen, were split into three categories (Classes 6, 7 and 9 in Table 1) based on the functional group to which oxygen attaches. In some cases, reactions in EC subclasses outside those listed above were assigned to classes of Table 1 (e.g., reaction R04059 in KEGG, which is assigned to EC 1.10.1.1, is included in Class 1). Also, Class 12 of Table 1 includes only reactions from EC 1.97, a catchall category for EC 1 reactions.

A.3. Reaction Center Patterns

A metabolite is a potential reactant in a reaction class only if it has structural features compatible with a class-specific reaction center. An example is shown in FIG. 1, which highlights a reaction center specific to Class 3 reactions. The reaction shown, R00408 in KEGG, is the reaction catalyzed by succinate dehydrogenase: succinate+FAD$^+$<=>FADH$_2$+fumarate. Indices are assigned to atoms, except for hydrogens.

Because the 12 reaction classes are defined on the basis of functional group transformations, each reaction in a class must involve a reaction center that corresponds to the functional group affected by the characteristic transformation of the class. For example, a substrate in a Class 1 reaction must have a functional group that qualifies it as a primary or secondary alcohol or a hemiacetal. Table 2 shows reaction centers and local structural motifs of substrates and products of the reactions listed in Table 1. As can be seen in Table 2, reaction centers are comprised of one to three atoms. The reaction centers highlighted in Table 2, like any molecular pattern in fact, can be precisely encoded using SMARTS strings. For example, the SMARTS string [C;!h0][Oh] encodes the first reaction center indicated in Table 2 (at top left). This pattern matches a hydroxyl group bound to a carbon atom of an alkyl group; thus, it can be used to identify alcohols. Reaction centers for all 1626 oxidoreductase-catalyzed reactions considered in Table 1 were manually identified and these reaction centers were encoded as SMARTS strings. Then, using a combination of expert knowledge and the results of graph mining (described below), more stringent structural requirements on the reactants in each reaction class were sought by inspecting the structures surrounding their reaction centers, looking for both typical and atypical features. SMARTS is a molecular substructure (patterns) modeling language.

Figure 2:
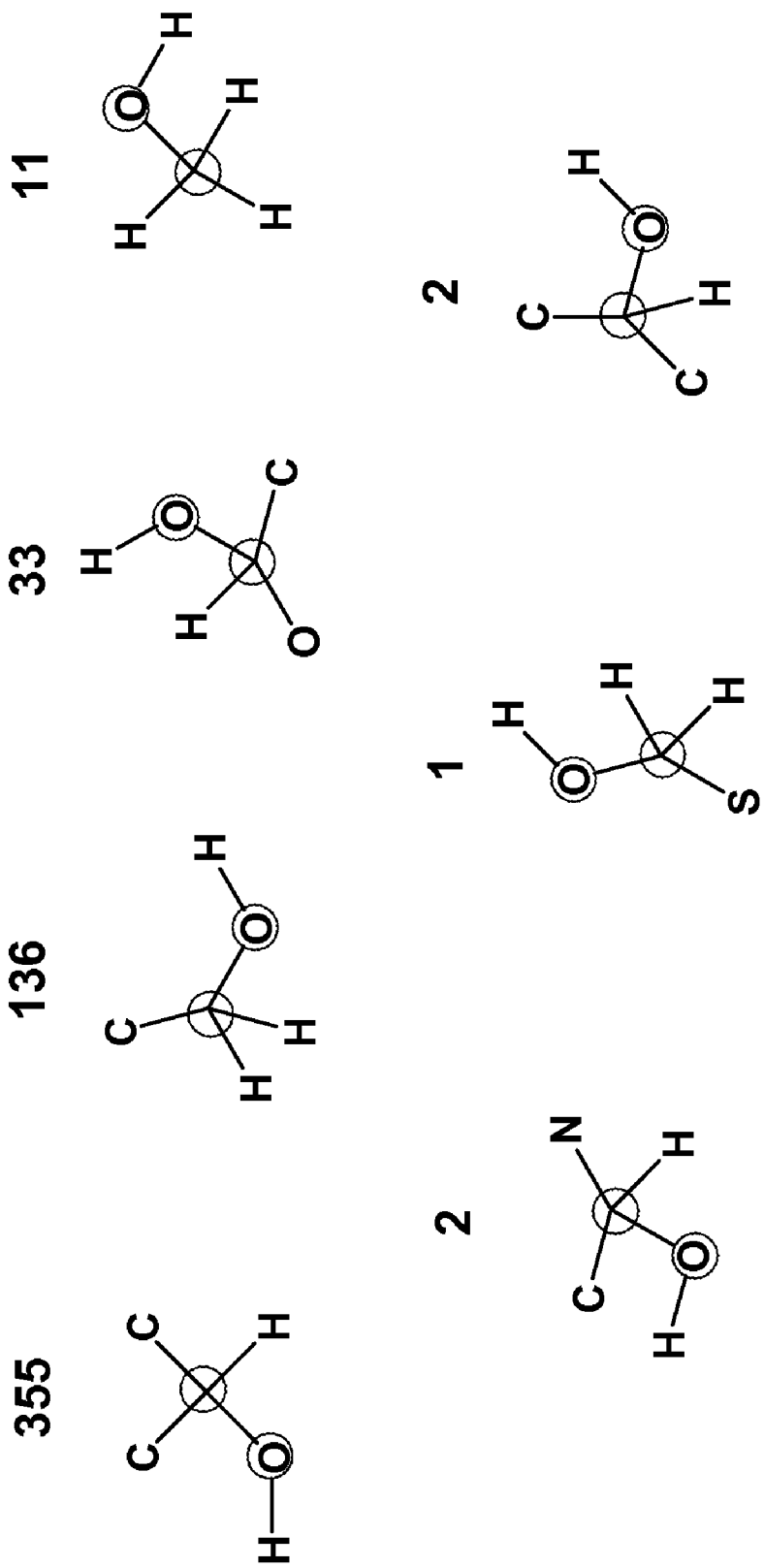
FIG. 2 illustrates seven distinct substructures found around certain reaction centers.

For each reaction center in a reaction, a breadth-first traversal of the graph corresponding to the chemical structure of each metabolite participating in the reaction—the substrate(s) and product(s) are considered in turn—was initiated. The traversal begins with the atoms of the reaction center. At each depth of the traversal, the substructure (the reaction center plus possibly some local surrounding structure) corresponding to the subgraph visited is stored. For example, for either the substrate or product of FIG. 1, Atoms 2 and 5 and the bond between them are stored at depth 0. This initial subgraph corresponds to the reaction center. Atoms 1 and 6 and the bonds that connect these atoms to the reaction center are added at depth 1, and all other atoms and bonds are added at depth 2. Traversal, even if extension is possible, is halted at depth 2. In this manner, 25 collections of reaction-center-containing substructures were obtained for the substrates and products of the 12 sets of reactions indicated in Table 1. A collection of substructures, which is one obtained for the substrates of the 540 reactions of Class 1, is illustrated in FIG. 2. These seven distinct substructures are found around the reaction centers (highlighted) of the 540 substrates of Class 1 reactions after a depth 1 breadth-first traversal starting from the reaction center. The number above each substructure indicates the number of substrates containing the substructure. The first six substructures, accounting for 538 out of 540 substrates, are matched by one of the two reaction center patterns defined in Table 2. The first, second, fourth, fifth and sixth substructures correspond to primary and secondary alcohols, which are matched by the SMARTS string [C;!h0;!$(C(O)O);!$(C=O)][Oh]. Note that, because Class 4 reactions have two products with distinct reaction centers, there are 25 rather than 24 collections. Each of the 25 collections was inspected and a set of patterns, encoded using SMARTS strings, was defined. These patterns, referred to as reaction center patterns, were selected with consideration of chemistry and with the goal of finding one or two patterns for each reaction class that together match as many of the known reactants in the corresponding class of reactions as possible. As described in more detail below, JOELib was used to perform SMARTS-based matching. The patterns defined through this process are illustrated in Table 2. There are one, one, and two reaction-center-containing substructures not matched by a pattern for reactions in Classes 1, 8, and 9, respectively. These rare substructures are found in only 10 metabolites. In some cases, a reaction center pattern encompasses only a reaction center. In other cases, the pattern extends beyond the reaction center, which suggests that the surrounding local structure is important for reactivity. Our assumption is that the reaction center patterns of Table 2, some of which include negative application conditions, represent structural motifs that are prerequisites for participation of a metabolite, as a substrate or product, in reactions of Classes 1-12.

A.4. Negative and Positive Examples For Training

Negative and positive examples are required to train a binary classifier through supervised learning. Using routines for SMARTS string matching in JOELib, the set of substructures among the 4139 metabolites in KEGG that contain each reaction center pattern of Table 2 was identified. In finding matches, routines in JOELib, based on Hückel's rule, were used to identify aromatic atoms and bonds, and the UniversalIsomorphismTester routine in CDK was used to avoid multiple matches to a single substructure because of symmetry. Each set of metabolite substructures was then divided into negative and positive examples. A substructure was considered to be a positive example if the metabolite containing it is documented in KEGG to participate in a reaction corresponding to the pattern the substructure matches. Other metabolite substructures were considered to be negative examples.

A.5. Atomic Properties/Descriptors

Classifiers map inputs to outputs. Here, the outputs of interest will indicate whether a metabolite is a substrate or product in a reaction of a given type. The inputs that were used in this illustrative embodiment are atomic properties, namely, a set of seven quantitative structure-property relationship (QSPR) empirical or semi-empirical descriptors calculated for each of the atoms in a reaction center. These descriptors were determined from 2D chemical structures using CDK and JOELib. Each descriptor is briefly described below.

Graph potential. This topological descriptor provides a measure of the distance of atoms from the graphical center of a molecule. Atoms that are close to the center will have a higher graph potential than atoms that are far from the center.

Electro-geometrical state index, electrotopological state index, and conjugated electrotopological state index. These three indices characterize the electronic state of an atom in the context of other atoms in a molecule.

Gasteiger-Marsili partial charges. Gasteiger-Marsili partial charges characterize the distribution of electrons in a molecule, which is one of the most important factors influencing its chemical properties. These partial charges are calculated through an iterative procedure that balances electronegativity of charge and charge transfer through electronegativity difference. The partial charge of an atom depends on both the type of atom and its molecular environment.

Effective polarizability. This property measures the effect of an electric field on the electron cloud of an atom.

Sigma electronegativity. This property reflects the electron-attracting ability of an atom in its molecular environment.

These descriptors were considered for two reasons. First, they measure topological and electronic properties, which were expected to be important for formation and breakage of covalent bonds. Second, these descriptors are readily calculated.

A.6. Classifiers

To predict the potential of a given metabolite to participate in an oxidoreductase-catalyzed reaction, binary classifiers were trained for each reaction class. The classification problem is to predict whether a metabolite matching a given reaction center pattern (i.e., containing a substructure with a potential reaction center plus possibly some additional surrounding local structure) is a substrate or product of a reaction of the type corresponding to the pattern. Classification is made on the basis of the QSPR descriptors listed above, which are calculated for each atom in the putative reaction center. Thus, in classification, from seven to 21 features of a metabolite are considered, depending on the number of atoms in the putative reaction center, which varies from one to three (Table 2). To establish a proof of principle and baseline performance expectations for a classifier, a predictor method was used that is both simple and computationally efficient: a linear-kernel Support Vector Machine (SVM). SVMs often perform well at classifying data not used in training (i.e., at generalization). Various kernels are popular. Nonlinear kernels, such as radial basis function (RBF) kernels, arguably offer the best SVM performance, although there is little theoretical guidance available about which kernel might be best for our problem. A linear kernel, corresponding to the simplest SVM, was used because this type of kernel has no adjustable parameters, and with this kernel, the weight vector w of the SVM (see below) provides a measure of which features have the most influence on classification outcome.

Figure 3:
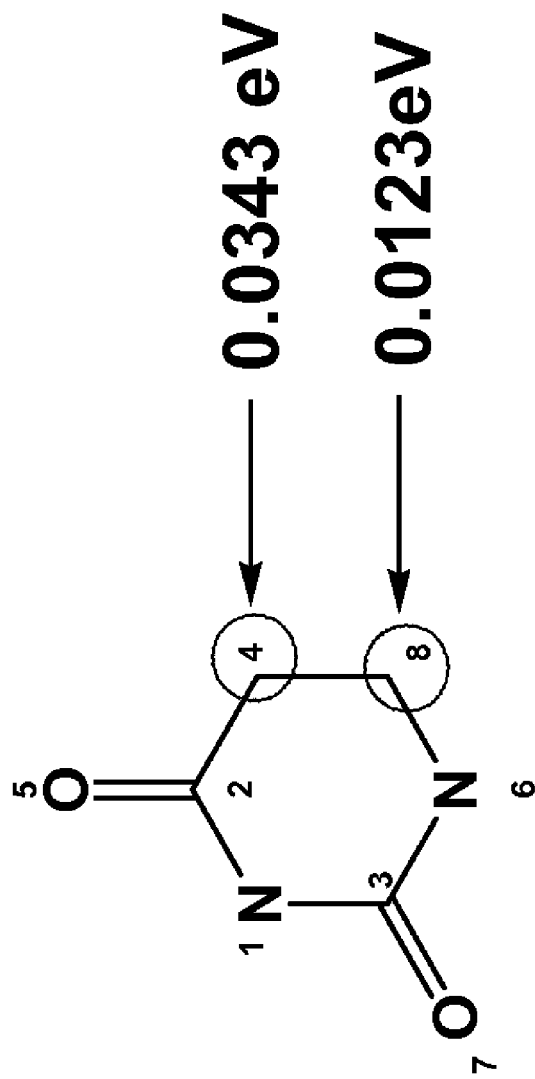
FIG. 3 shows the atoms in a symmetric reaction center.

Twenty five (25) training sets were considered, one (or two in one case) for each entry in Table 2, as discussed above. Each metabolite substructure i in a training set has an output $y_i = \{-1, 1\}$, depending on whether the metabolite substructure is a negative (−1) or positive (1) example. Each metabolite substructure is also associated with an input vector $x_i = (x_{i1}, \ldots, x_{id})$, which is based on the atomic properties discussed above. Unadjusted values of inputs can be on different scales. The inputs $x_{ij}$ were linearly scaled such that $\min_i x_{ij} = -1$ and $\max_i x_{ij} = 1$ for any given j. The length of the input vector, d, is the product of the number of atomic properties considered (7) and the number of atoms (from 1 to 3) in the reaction center associated with the training set of interest. The elements of the input vector are ordered according to the corresponding reaction center pattern, in which atoms in the reaction center are specified to have a fixed, arbitrary ordering. For symmetric reaction centers, elements of the input vector are further ordered according to a metabolite-specific ordering of atoms in the reaction center, which is illustrated in FIG. 3. Atoms in a symmetric reaction center (matched by the first substrate pattern of Class 3 reactions) are highlighted. Although the reaction center is symmetric, Atoms 4 and 8 are distinct because of their different chemical environments. Atoms in this reaction center, and all other symmetric reaction centers, are ordered based on their Gasteiger-Marsili partial charges, from most negative to most positive. Thus, Atom 8, which has partial charge 0.0123 eV, comes before Atom 4, which has partial charge 0.0343 eV.

Given inputs $x_i$ and output $y_i$ for all i in a training set, the idea of a linear SVM is to find a hyperplane in the space of inputs x, satisfying the equation $w^T x + b = 0$, that splits the negative and positive examples with maximum margin. The margin of a separating hyperplane is the width by which it can be increased before touching a data point. The parameters of the SVM include the vectors w and b. Additional parameters include slack variables $\xi_i$ and two penalty parameters $C_-$ and $C_+$. The slack variables, which introduce a soft margin, are included to account for negative and positive examples that are not linearly separable, and the penalty parameters are included to effectively balance unequal numbers of negative and positive examples. For simplicity the following relations were used to specify the penalty parameters: $C_-=1$ and $C_+=N_n/N_p$, where $N_n$ is the number of negative examples in a training set and $N_p$ is the number of positive examples. The other parameters are found by solving a minimization problem:

$$\min_{w,b,\xi} \frac{1}{2} w^T w + C_+ \sum_{y_i=1} \xi_i + C_- \sum_{y_i=-1} \xi_i$$

Minimization is subject to the following constraints:

$$y_i(w^T x_i + b) \geq 1 - \xi_i$$

and $$\xi_i \geq 0, \forall i$$

SVMs found as indicated above are used as follows. Given a SVM with parameters w and b and a metabolite substructure with inputs $x_i$, calculate the quantity $w^T x_i + b$. If the sign of this quantity is positive, the metabolite is predicted to be reactive in the type of reaction corresponding to the SVM. Conversely, if the sign is negative, the metabolite is predicted not to be reactive.

To measure the performance of a SVM, count the numbers of true positives (TP), true negatives (TN), false positives (FP), and false negatives (FN) that it predicts for test data. Then calculate two ratios: sensitivity, which is the fraction of positive examples that are predicted to be positives, $Q_p$=TP/(TP+FN), and specificity, which is the fraction of negative examples that are predicted to be negatives: $Q_n$=TN/(TN+FP). These quantities are calculated as part of a 10-fold cross validation (CV) procedure. In the CV procedure, the relevant training data set is divided randomly into 10 equal sets. Then, each of the 10 sets is used for testing while the other nine sets are used for training. In a sensitivity analysis, the number of negative examples included in training sets were varied, randomly excluding some fraction. Each of the above procedures was repeated 10 times; the mean values of $Q_p$ and $Q_n$ were determined in each case.

B. Results

As described above, binary classifiers were developed for predicting the reactivity of potential substrates and products in the 12 classes of oxidoreductase-catalyzed reactions defined in Table 1. A potential substrate or product is a metabolite that contains a substructure matching one of the reaction center patterns defined in Table 2 and is classified as reactive or not reactive in the corresponding type of reaction based on seven QSPR descriptors for each atom in the putative reaction center. These descriptors provide a characterization of the electronic and topological atomic properties of the potential reaction center. The accuracy of predictions was assessed by ten-fold cross validation. Results are shown in Table 3, which illustrates the performance of classifiers at making predictions according to the invention.

The quality of a classifier was measured by its sensitivity, $Q_p$, and specificity, $Q_n$. The average sensitivity and specificity obtained for 10 sets of tests in a 10-fold cross validation (CV) procedure are given for each classifier in Table 3, which also indicates the numbers of positive and negative examples used in each of the training sets. Sensitivity ranges from 64% to 93% for substrates and from 71% to 98% for products. Specificity ranges from 44% to 92% for substrates and from 50% to 92% for products. The standard deviation (not shown) is always small, being less than 0.03 for all cases. The substrate and product classifiers for a given type of reaction vary in performance because these classifiers were derived independently using distinct training sets.

Figure 4:
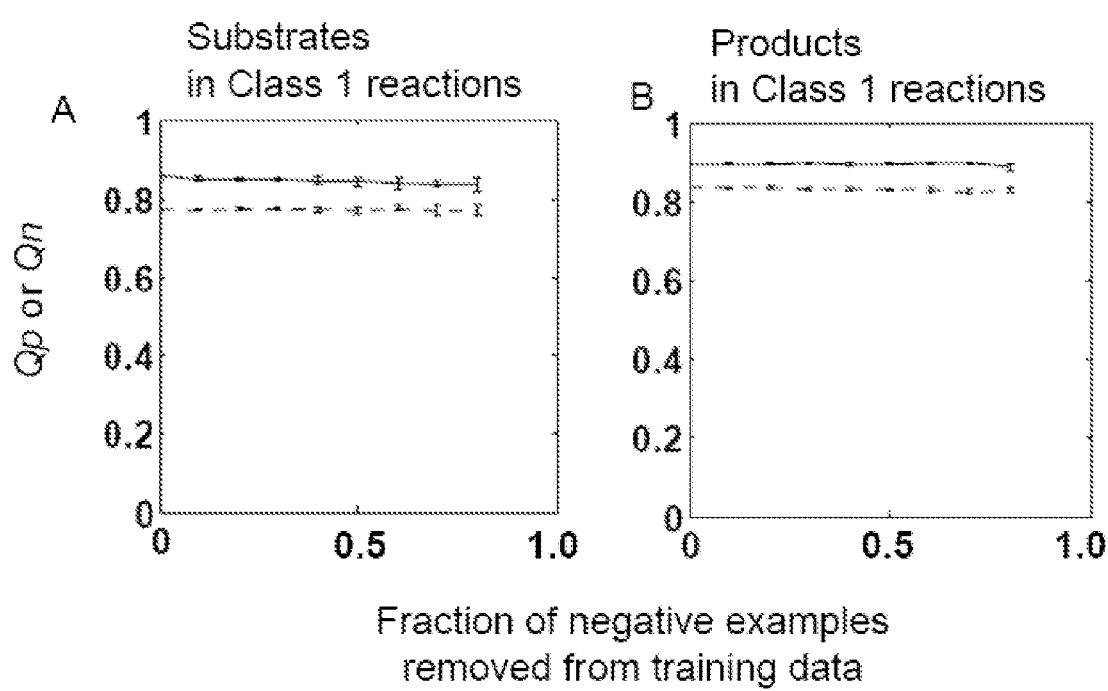
FIG. 4 illustrates classifier performance as negative examples are removed from training data.

In training a classifier for a particular type of reaction, metabolites in the KEGG database not known to participate in that type of reaction were used as negative examples. However, our knowledge of metabolism is incomplete, and some of these putative negative examples might actually be positive examples. Moreover, negative examples include only metabolites that are substrates and/or products of known enzymatic reactions, which might weaken the ability of a classifier to generalize when applied to xenobiotic compounds or novel metabolites. To determine how classifier sensitivity and specificity depend on the negative examples included in a training set, a fraction of the negative examples, which were randomly selected, were removed, and the analysis of Table 3 was repeated. Fractions of different sizes were removed. Results for classifiers of potential substrates and products in Class 1 reactions are shown in FIG. 4. Classifier performance remains steady as negative examples are removed from training data. The horizontal axis indicates the fraction of negative examples removed (randomly). The classifiers considered here predict the reactivity of potential substrates (left panel) and products (right panel) in Class 1 reactions. Mean values and standard deviations are indicated for $Q_p$ (solid line) and $Q_n$ (broken line), which are calculated from 10 tests in a 10-fold CV procedure. These results, which indicate that sensitivity and selectivity are robust to variations of the training data, are typical.

Figure 5:
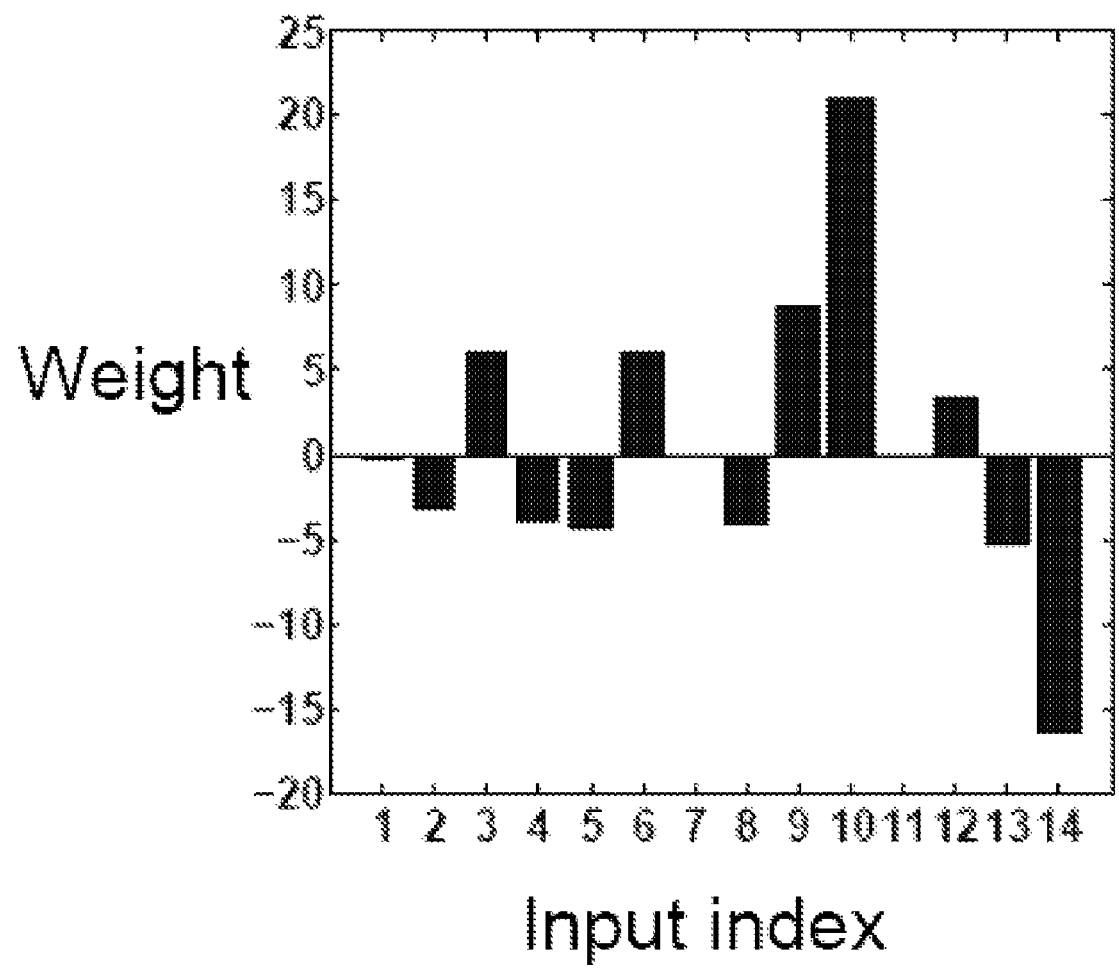
FIG. 5 shows the weight parameter distribution for a SVM classifier.

To determine the properties of reaction centers that are most relevant for predicting reactivity, the weight parameters w of a classifier can be used to rank the relative importance of its inputs x. The inputs weighted most heavily are most informative. FIG. 5 shows the weight parameter distribution of the (linear-kernel SVM) classifier for substrates of Class 3 reactions, in which a CH—CH group is dehydrogenated with the introduction of a double bond. The reaction center associated with this reaction class (CH—CH) is comprised of two carbon atoms. Thus, there are 14 inputs, $x_1, \ldots, x_4$, the indices of which are indicated on the horizontal axis, and the same number of weights, the values of which are indicated on the vertical axis. Odd indices of inputs correspond to the first atom in the reaction center, whereas even indices correspond to the second atom. Recall that ordering of atoms in a reaction center is determined as described above (A.6.). The first inputs considered (at left) are graph potentials. The other inputs are considered in the same order as they are listed above (A.5.). Thus, the ninth and tenth inputs correspond to Gasteiger-Marsili partial charges of the first and second atoms, respectively. These inputs are associated with the two largest positive-valued weights (i.e., the tallest bars in the plot). As a result, a metabolite with larger, more positive partial charges will be more likely to be classified as a true substrate than one with smaller, more negative charges. As can be seen, the Gasteiger-Marsili partial charges of the two carbon atoms in the CH—CH reaction center are responsible for the largest positive contributions to the classifier output. This result suggests that reactivity requires a deficiency of electrons in the reaction center, which is consistent with chemical intuition. However, in general, there is no easily discernible chemical interpretation of the weight distribution of a classifier.

C. Alternate Embodiments, Generalizations and Conclusions

The illustrative embodiment of the invention described above has provided binary classifiers, linear-kernel SVMs, that predict whether a potential substrate or product in one of 12 types of oxidoreductase-catalyzed reactions is a true reactant or not. The classifiers require structural information but no genomic sequence information. A 10-fold cross validation procedure was used to assess the performance of each classifier. Typically, but not uniformly, both high sensitivity and specificity are found (Table 3), which suggests that the classifier inputs reflect the ability of a metabolite to participate in an oxidoreductase-catalyzed reaction in many cases. These inputs are descriptors of the topological and electronic properties of atoms in the potential reaction center. The overall results establish the feasibility of the approach and baseline performance expectations, and the invention may be implemented in more sophisticated classifiers. For example, classifiers can use SVMs based on nonlinear kernels. A nonlinear kernel, such as a radial basis function or polynomial kernel, should, with careful selection of kernel parameters, perform better than a linear-kernel SVM.

In cases where sensitivity or specificity is less than satisfactory, the particular descriptors utilized may simply be uninformative, in which case additional descriptors and/or more relevant or predictive descriptors might yield better results. Alternatively, it may be that reactivity is determined not by metabolite structure alone but rather by enzyme properties or conformational changes induced by enzyme-substrate binding. The influence of enzyme-dependent properties on reactivity can be difficult to assess, but more predictive descriptors of atomic and molecular properties can be obtained through straightforward application of quantum chemistry methods, which require a 3D chemical structure. The drawback of these methods is that they are more computationally expensive and technically challenging than the ones used here. However, again, the overall results leads to extension of the invention, including the consideration of more expensive calculations of metabolite features.

An advantage of the prediction system presented here over earlier rule-based approaches is the quantitative and automatic assessment of the reactivity of a given metabolite, beyond a checking of the structural requirements of a transformation rule. Thus, experimental follow up can be focused faster on fewer metabolites, those with atomic properties characteristic of known reactants. The development of the methods presented here, which have been applied to a single EC class of enzyme-catalyzed reactions but can be extended systematically to the other five major EC reaction classes and beyond, represents a step toward the development of computational screening tools that can aid in elucidating the functional roles of newly discovered small-molecule metabolites.

The KEGG database contains reactions catalyzed by various classes of enzymes: oxidoreductases (EC1), transferases (EC2), hydrolases (EC3), lyases (EC4), isomerases (EC5), ligases (EC6), plus reactions without EC number. FIG. 6A-F are tables of the classification of enzyme-catalyzed reactions based on functional group chemistry for each of the EC numbers. Table 1 is a subset of FIG. 6A for EC1, selected as previously described. Most of the reactions without an EC number can be fit into one of these six groups. The invention can be carried out with these other enzyme-catalyzed reactions by applying the principles illustrated above and described more generally below. Reaction data from other databases than the KEGG database can also be used, for example, the Molecular Design Ltd (MDL) Metabolite® and Accelrys' Metabolism databases, which are primarily for drugs, and the University of Minnesota Biocatalysis/Biodegradation database, which is special for biodegradation and bioremediation reactions.

Transferases (EC2) reactions can be represented as A-X+B→A+B—X where X is the functional group to transfer, A is the group donor and B is the group acceptor. The biotransformation B→B—X and A→A-X is used to represent the transferases reactions. 26 subclasses has been defined for EC2 reactions based on the functional group X to be transferred and the accepting functional group in group acceptor A or B. Hydrolases (EC3) reactions can be represented as A-B+$H_2O$→A-OH+B—H. For these reactions there are two separate compounds as products, so they are analyzed separately. 19 subclasses have been defined for EC3 reactions based on the type of chemical bond to be hydrolyzed. Lyases (EC4) is classified into 7 subclasses based on the type of chemical bonds cleaved and type of new bonds formed. Isomerases (EC5) are classified into 3 subclasses based on the type of conversion. Four subclasses are defined for ligases (EC6) reactions based on the type of formed chemical bond. For the EC1-EC6 reaction classes, the total number of biotransformation classes is 80.

FIG. 6G-L illustrate biotransformations for each of the six EC classes. FIG. 6G shows the reaction center structure for reactants of aromatic dioxygenation (decyclizing) reactions, an EC1 reaction. The reaction centers are two aromatic carbons and specific local structures around the reaction center is required for this type of reaction to occur. It can be divided into three types: type A and B performs intradiol- and extradiol-cleaving of catechol, and type C performs indole and similar ring cleaving. FIG. 6H shows the O-methyl-transformation, an EC2 reaction. FIG. 6I shows linear carboxylic ester hydrolization, an EC3 reaction. For this reaction, two distinct products exist and they are analyzed separately. FIG. 6J shows decarboxylation reaction, an EC4 reaction. $CO_2$ is a product of this reaction. Because it is consistent among all reactions, it is ignored in the biotransformation. FIG. 6K shows the reaction of transposing C=C, an EC5 reaction. The reactant and product are analyzed together for this reaction. FIG. 6L shows the reaction of acid-ammonia, amine or amino ligases, an EC6 reaction.

Figure 7C:
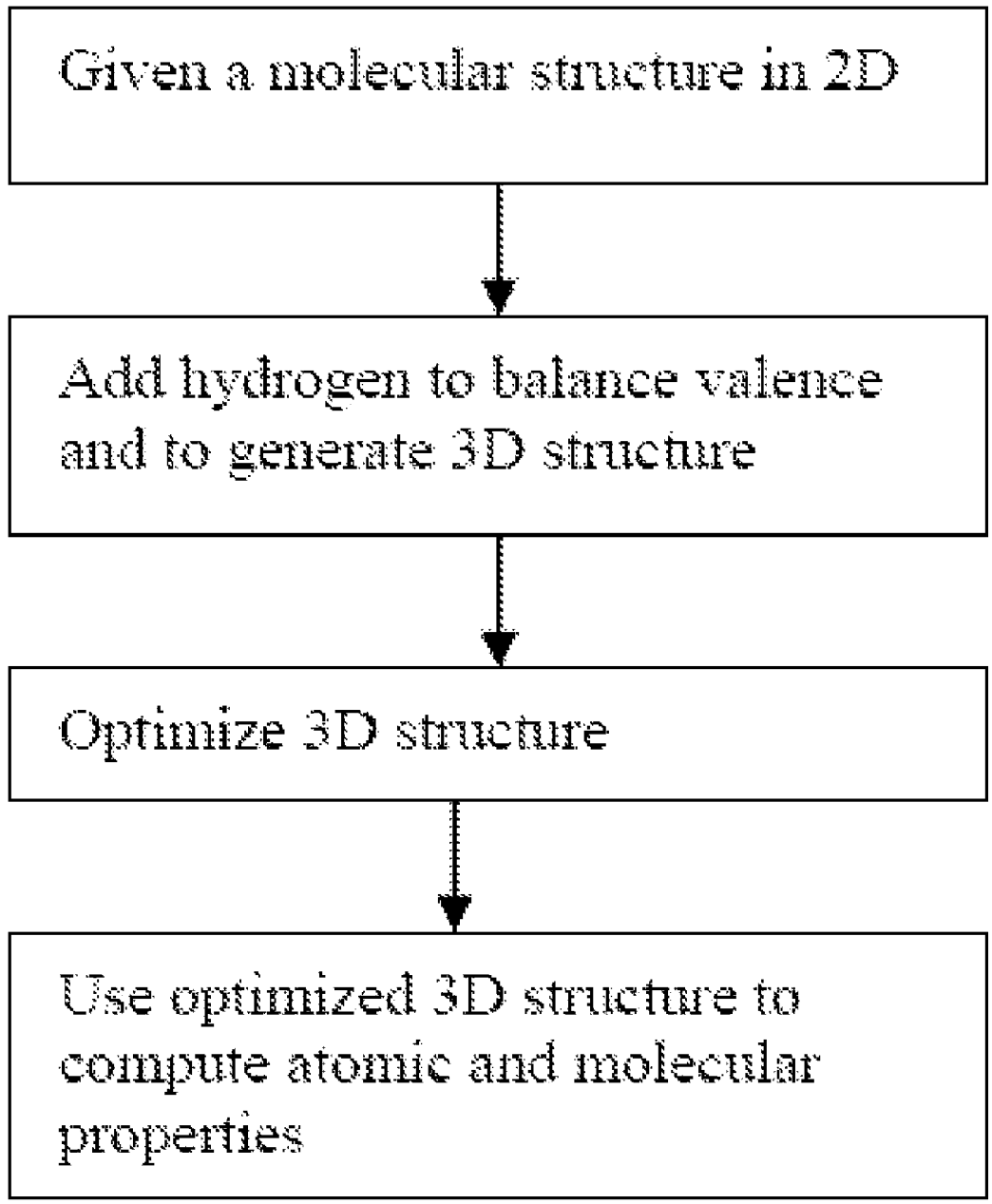
FIG. 7C is a flowchart of a process for obtaining 3D structure from 2D structure.

While a particular set of seven atomic property descriptors were utilized in the illustrative embodiment, and worked well, other descriptors can also be used in other situations. FIG. 7A is a list of atomic properties (21) and FIG. 7B is a list of molecular properties (42) that could be considered. The atomic properties include 6 that use 2D information and the rest 3D; 9 properties are based on quantum chemistry. Atomic properties include electric, energetic, steric and topological properties. A more complex implementation of the invention could use all 21+42 properties, and even additional properties such as geometrical distance and atom depth. Some properties require 3D structure. FIG. 7C is a flowchart of a process for obtaining 3D structure from 2D structure. The process can be carried out with well-known chemical software, e.g. MolConverter for generating 3D structure, MOPAC 2002 for optimizing the 3D structure, and JOELib, CDK and MOPAC 2002 for computing properties.

Figure 8:
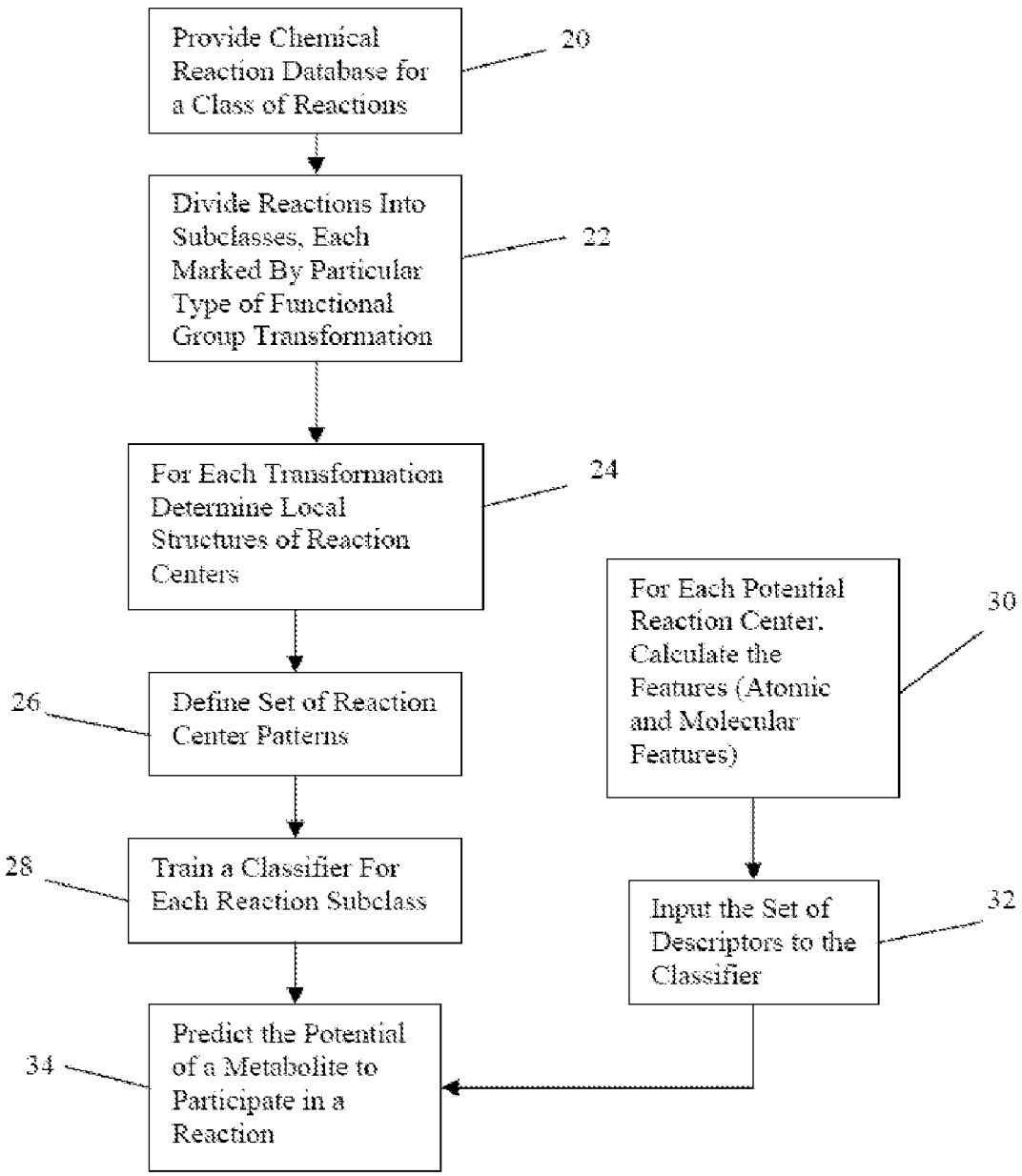
FIG. 8 is a flowchart of the method of the invention.

The method of the invention is more broadly shown in the flowchart of FIG. 8. In step 20, one provides or obtains a chemical reaction database for a class of reactions (e.g. KEGG database for enzyme-catalyzed reactions.) In step 22, the reactions are divided into reaction subclasses, each marked by a particular type of functional group transformation (e.g. oxidoreductase-catalyzed reactions.) For each transformation (reaction subclass), the local structures of the reaction centers are determined, step 24. This is done for all the substrates and products of the set of reactions in the subclass. A set of reaction center patterns is then defined from the reaction center structures, step 26. The reaction center patterns are chosen to best match as many of the known reactants in the corresponding reaction subclass as possible.

A classifier (e.g. SVM) is then trained for each reaction subclass, step 28. This requires both negative and positive examples, as described previously (A.4.). For each reaction center, a set of features (or descriptors) which are selected from atomic and molecular features are calculated, step 30, and the descriptors are input into the trained classifier, step 32. The trained classifier predicts the potential of a metabolite to participate in a reaction from the calculated descriptors, step 34. Steps 28, 30, 32, 34 are more generally the step of determining if the metabolite is a potential reactant in a subclass by determining if it has structural features compatible with a subclass-specific reaction center using a trained classifier.

Figure 9:
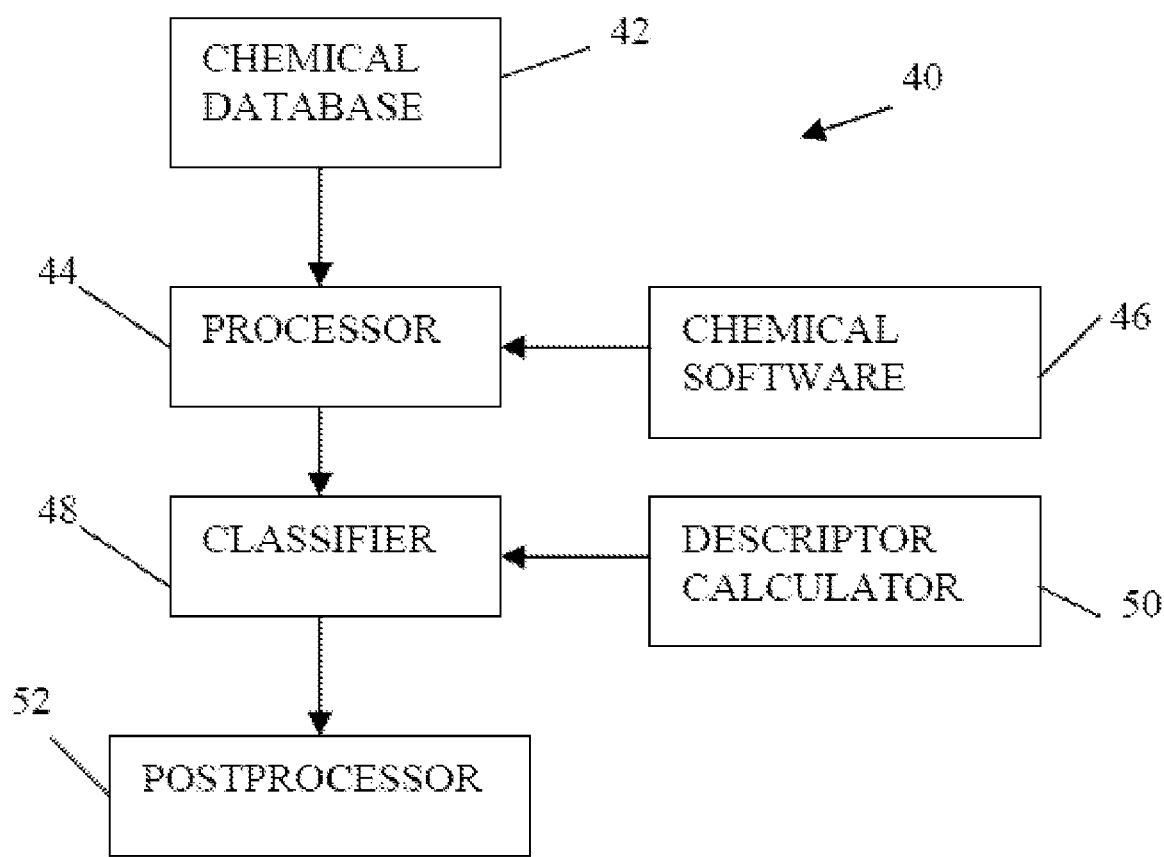
FIG. 9 is a diagram of a system for carrying out the invention.

The invention may be carried out with a variety of systems, one configuration of which is shown in FIG. 9. System 40 is connected to or in some way accesses information in a chemical reaction database 42. The data from database 42 is processed by processor 44, e.g. a digital computer, which operates using various chemical software packages 46, such as CDK and JOELib, which are readily available open source programs. Processor 44 is used to obtain the reaction center structure and pattern data from the reaction data from database 42. The output from processor 44 is input into classifier 48, e.g. a SVM, for training the classifier. A descriptor calculator 50 calculates the set of chemical features, selected from atomic properties of the atoms in the reaction center and molecular properties, and inputs them into the classifier 48. A postprocessor 52 may be used to produce a probability. This particular configuration is illustrative only; any apparatus that can carry out the functions can be used. For example, processor 44 and calculator 50 may not be separate components but may be parts of digital computer. The components need not be physically located together; for example, database 42 may be remotely located from processor 44 and accessed online.

The invention provides a useful quantitative and automatic predictor of metabolic reactivity from the presence or absence of local structural motifs in compounds and their readily calculated atomic and molecular features. This ability is important to the pharmaceutical and agricultural industries as well as many others. Greater capability for predicting a given metabolic transformation can reduce investigative costs and development time for pharmaceuticals or agricultural pesticides. The demonstrated accuracy of prediction is sufficient so that experimental follow up can be focused faster on fewer metabolites.

The usefulness or application of the invention depends on the training data. There are many potential sources of training data beyond the KEGG database. For example, there are databases that collect information about man-made chemicals. These databases could be used to predict enzyme-catalyzed reactions of xenobiotic compounds, which could be useful for engineering microorganisms or communities of organisms to have metabolic capabilities needed for bioremediation purposes. Likewise, databases collecting information about drugs could be used to predict drug toxicity arising from drug metabolism.

Thus the invention can be used in two different ways, training a classifier to distinguish between compounds that are likely and unlikely to participate in an enzyme-catalyzed reaction leading to a given functional group transformation, and using the trained classifiers to predict reactions for specific purposes, to determine drug toxicity or bioremediation properties.

The chemical structure of a drug candidate is used to calculate a set of chemical features. Based on these features, a set of trained classifiers (obtained by using drug compound training data) is used to determine the likely metabolic breakdown products. The method can be iterated to predict further breakdown products. Knowledge of the likely breakdown products is useful, because one can look among the predicted products for signatures of toxicity.

Another application of the method is to use it to predict reactions of man-made chemicals that are environmental pollutants. Again, from the chemical structure of a pollutant, a set of chemical features is calculated. Based on these features, a set of trained classifiers (obtained using xenobiotic compound training data) is used to determine the possible biotransformations. Knowledge of possible biotransformations can be used to determine the metabolic capabilities required to convert a pollutant from a toxic chemical to one that is safe for the environment. A microorganism can then be engineered to express the enzymes with the necessary metabolic capabilities or a community of organisms with the required capabilities can be designed for bioremediation purposes.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

TABLE 1

| Class of reaction | Description | Predominant EC 1 subclass | Number of reactions |
|---|---|---|---|
| 1 | Dehydrogenation of alcohols or hemiacetals | 1.1.-.- | 540 |
| 2 | Oxidation of an aldehyde or ketone | 1.2.-.- | 182 |
| 3 | Dehydrogenation of a CH—CH group introducing a double bond | 1.3.-.- | 217 |
| 4 | Oxidation of an amine yielding an imine which hydrolyzes to an aldehyde or ketone | 1.4.-.- | 123 |
| 5 | Dehydrogenation of an amine introducing a C=N double bond | 1.5.-.- | 39 |
| 6 | Oxidation of a C—H to generate a C—OH | 1.14.-.- and 1.17.-.- | 265 |
| 7 | Oxidation of C=C to generate C(OH)—C(OH) | 1.14.-.- | 65 |
| 8 | Breaking a C—C bond | 1.13.-.- | 77 |
| 9 | Breaking a C—C bond | 1.14.-.- | 57 |
| 10 | Oxidation of a nitrogenous group | 1.7.-.- | 27 |
| 11 | Oxidation of thiols with formation of a disulfide bond (S—S) | 1.8.-.- | 30 |
| 12 | Oxidation introducing a C-halide group | 1.97.-.- | 17 |

TABLE 2

| Class of reaction | Reaction center patterns for reactants | Reaction center patterns for products |
|---|---|---|
| 1 | H-C(-OH)[!-O, !=O] or HO-C(H)(-C)-O-C | C=O or C(-OH)(-O-C)[C,H] |
| 2 | O=C-H or O=C(-H)(-C=O) | [C,c]—[O,o] with C=O, or C(=O)—S |
| 3 | H-C-C-H or H-C(-C(=O)-OH) | C=C or c≐c |
| 4[#] | H-C[N,n] or C=N | C=O + N |
| 5 | H-C-N | C=N or c≐n |
| 6 | H-C-H [!=O, !-O] or C—H | [!-O]-[C,c]-O or c-O-H |
| 7 | C=C or c≐c | C-C with [—O,=O] [—O,=O] (epoxide-like) |
| 8[$] | c≐c or C=C | [C,c]=O or c—O |
| 9[$] | [C,c]—C[—Oh,=O] | C=O or [C,c]-O-[H,C] |
| 10 | N | N—OH or N=O or O=N—O |
| 11[&] | S—H | S—S |
| 12 | C—H or C=C—H | [C,c]—[Cl,Br,I] |

* In patterns, aromatic atoms are indicated by lower case letters, and aromatic bonds are indicated by broken lines (---) The symbol "!" denotes a negative application condition, i.e., a condition that prevents a match. For example, "!=O" indicates "not doubly bound to oxygen."
[#]Reactions in Class 4 have two products, which have distinct reaction centers.
[$]Reactions in Classes 8 and 9 have two products, which have indistinguishable reaction center patterns.
[&]Reactions in Class 11 have two substrates, which have indistinguishable reaction center patterns.

TABLE 3

| Class of reaction | Predictions based on reaction center patterns of substrates | | | | Predictions based on reaction center patterns of products | | | |
|---|---|---|---|---|---|---|---|---|
| | Training set | | CV performance | | Training set | | CV performance | |
| | Pos. | Neg. | $Q_p$ | $Q_n$ | Pos. | Neg. | $Q_p$ | $Q_n$ |
| 1 | 538 | 4140 | 0.87 | 0.77 | 539 | 4498 | 0.89 | 0.83 |
| 2 | 182 | 209 | 0.82 | 0.75 | 182 | 2256 | 0.80 | 0.74 |
| 3 | 217 | 17143 | 0.72 | 0.69 | 217 | 10412 | 0.76 | 0.66 |
| 4 | 123 | 2618 | 0.85 | 0.80 | 123 | 4203 | 0.90 | 0.89 |
| | | | | | 50 | 2490 | 0.90 | 0.77 |

TABLE 3-continued

| | Predictions based on reaction center patterns of substrates | | | | Predictions based on reaction center patterns of products | | | |
|---|---|---|---|---|---|---|---|---|
| Class of | Training set | | CV performance | | Training set | | CV performance | |
| reaction | Pos. | Neg. | $Q_p$ | $Q_n$ | Pos. | Neg. | $Q_p$ | $Q_n$ |
| 5 | 39 | 2178 | 0.93 | 0.78 | 39 | 4328 | 0.95 | 0.83 |
| 6 | 263 | 21766 | 0.78 | 0.44 | 265 | 13821 | 0.84 | 0.75 |
| 7 | 65 | 10504 | 0.85 | 0.75 | 65 | 6061 | 0.93 | 0.92 |
| 8 | 77 | 10479 | 0.86 | 0.85 | 149 | 6119 | 0.91 | 0.86 |
| 9 | 57 | 11070 | 0.87 | 0.80 | 111 | 16248 | 0.85 | 0.85 |
| 10 | 23 | 2858 | 0.64 | 0.92 | 27 | 73 | 0.72 | 0.84 |
| 11 | 60 | 34 | 0.78 | 0.53 | 30 | 10 | 0.98 | 0.50 |
| 12 | 17 | 6865 | 0.66 | 0.84 | 17 | 176 | 0.71 | 0.80 |

What is claimed is:

1. A method of predicting the reactivity of a metabolite, comprising:
using a processor and software executable on the processor, performing steps comprising:
obtaining information about a class of metabolic chemical reactions;
dividing the class of reactions into a plurality of subclasses, each marked by a particular type of functional group transformation;
determining local structures of metabolite reaction centers for each transformation;
defining a set of reaction center patterns from the local structures; and
determining if the metabolite is a potential reactant in a subclass by determining if it has structural features compatible with a subclass-specific reaction center using a trained classifier.

2. The method of claim 1, wherein determining if the metabolite is a potential reactant in a subclass by determining if it has structural features compatible with a subclass-specific reaction center using a trained classifier comprises:
training a classifier for each transformation;
calculating a set of descriptors selected from atomic properties for each atom in a reaction center and molecular properties;
inputting the set of descriptors to the classifier; and
predicting the reactivity of the metabolite to participate in a reaction.

3. The method of claim 1, wherein the class is enzyme-catalyzed reactions.

4. The method of claim 3, wherein one subclass is oxidoreductase-catalyzed reactions.

5. The method of claim 2, wherein the class is enzyme-catalyzed reactions.

6. The method of claim 5, wherein one subclass is oxidoreductase-catalyzed reactions.

7. The method of claim 1, wherein the reaction center patterns are selected to match as many known reactants in the corresponding subclass as possible.

8. The method of claim 2, wherein the reaction center patterns are selected to match as many known reactants in the corresponding subclass as possible.

9. The method of claim 2, wherein the classifier is trained by providing positive and negative examples.

10. The method of claim 9, wherein positive and negative examples are provided by identifying a set of structures among the metabolites in the class of metabolite reactions that contain each reaction center pattern and considering a structure to be a positive example if the metabolite containing it is known to participate in a reaction corresponding to the reaction center pattern the structure matches and considering it a negative example if it is not so known.

11. The method of claim 2, wherein the classifier is a support vector machine.

12. The method of claim 11, wherein the classifier is a linear-kernel support vector machine.

13. The method of claim 2, wherein the descriptors are atomic properties.

14. The method of claim 13, wherein the atomic properties include electric, energetic, steric and topological properties.

15. The method of claim 13, wherein the atomic properties are graph potential, electrogeometrical state index, electrotopological state index, conjugated electrotopological state index, Gasteiger-Marsili partial charges, effective polarizability, and sigma electronegativity.

16. The method of claim 13, further comprising molecular properties.

17. A system for predicting the reactivity of a metabolite, comprising:
a processor for (i) receiving information about a class of metabolic chemical reactions, (ii) dividing the class of reactions into a plurality of subclasses, each marked by a particular type of functional group transformation, (iii) determining local structures of metabolite reaction centers for each transformation, and (iv) defining a set of reaction center patterns from the local structures;
a classifier for predicting the reactivity of the metabolite to participate in a reaction, the classifier having been trained for each transformation; and
a descriptor calculator for calculating a set of descriptors selected from atomic properties for each atom in a reaction center and molecular properties, the set of descriptors being input to the trained classifier.

18. The system of claim 17, wherein the classifier is a support vector machine.

19. The system of claim 17, wherein the descriptors are atomic properties.

20. A system for predicting the reactivity of a metabolite, comprising:
a processor for (i) receiving information about a class of metabolic chemical reactions, (ii) dividing the class of reactions into a plurality of subclasses, each marked by a particular type of functional group transformation, (iii) determining local structures of metabolite reaction centers for each transformation, and (iv) defining a set of reaction center patterns from the local structures; and
means for determining if the metabolite is a potential reactant in a subclass by determining if it has structural features compatible with a subclass-specific reaction center.

* * * * *